United States Patent [19]

Neri et al.

[11] Patent Number: 4,562,266

[45] Date of Patent: Dec. 31, 1985

[54] PROCESS FOR THE PREPARATION OF 2,3-DIHYDRO-2,2-DIMETHYL-7-BENZOFURANOL

[75] Inventors: Carlo Neri; Villiam Giroldini, both of S. Donato Milanese; Mario Traversoni, Osio Sotto; Guido Guizzi, Milan; Emilio Perrotti; Antonio Rinaldi, both of S. Donato Milanese, all of Italy

[73] Assignee: Enichimica Secondaria, S.p.A., Palermo, Italy

[21] Appl. No.: 602,214

[22] Filed: Apr. 19, 1984

[30] Foreign Application Priority Data

Apr. 22, 1983 [IT] Italy ............................. 20738 A/83
Apr. 22, 1983 [IT] Italy ............................. 20739 A/83

[51] Int. Cl.$^4$ ........................................ C07D 307/86
[52] U.S. Cl. ................................. 549/462; 568/727
[58] Field of Search ........................................ 549/462

[56] References Cited

U.S. PATENT DOCUMENTS 4,118,400 10/1978 Michaely .......................... 549/462

FOREIGN PATENT DOCUMENTS 2525598 10/1983 France .......................... 549/462

Primary Examiner—Richard A. Schwartz
Assistant Examiner—Bernard I. Dentz
Attorney, Agent, or Firm—Hedman, Gibson, Costigan & Hoare

[57] ABSTRACT

Process for the preparation of 2,3-dihydro-2,2-dimethyl-7-benzofuranol, comprising the reaction between catechol or 4-tert.butyl catechol and isobutyraldehyde in the presence of catalytic amounts of at least one compound selected from the group consisting of the oxides, hydroxides, alcoholates and carboxylates of metals belonging to the Groups IA, IIA, IIB and VIIB of the Periodic System of the Elements and the subsequent reaction of rearrangement of the products which have been obtained, optionally previously removing one or more low-boiling components, in the presence of a compound having acidic properties, of an organic or a mineral nature. The product is useful in the synthesis of pesticides.

15 Claims, No Drawings

PROCESS FOR THE PREPARATION OF 2,3-DIHYDRO-2,2-DIMETHYL-7-BENZOFURANOL

FIELD OF THE INVENTION

This invention relates to a process for the preparation of 2,3-dihydro-2,2-dimethyl-7-benzofuranol.

The compound 2,3-dihydro-2,2-dimethyl-7-benzofuranol is an appreciable intermediate, which is especially useful for the synthesis of 2,3-dihydro-2,2-dimethyl-7-benzofuranyl carbamate, a powerful pesticide known under the Trade Name of CARBOFURAN.

BACKGROUND OF THE ART

A number of processes are known in the art for the production of 2,3-dihydro-2,2-dimethyl-7-benzofuranol.

It is known, for example, to interact o-nitrophenol with metallyl chloride, subsequently effecting the Claisen transposition of the phenolic ether thus obtained, and the further conversion of the nitro group into a hydroxyl group, as disclosed in the U.S. Pat. No. 3,320,286.

Such a process has shortcomings connected with its intricacy and the high costs of the requested raw materials.

Another process comprises the step of interacting catechol with metallyl chloride to give 2-oxymetallylphenol, the latter being subsequently subjected to Claisen transposition, optionally under the influence of acidic catalysts, such as disclosed, for example, in the German Patent Application No. 2,932,458 and the European Published Application No. 40,400. This process mainly exhibits the drawbacks deriving from the low selectivity of the useful reaction product and the high cost of metallyl chloride. Another process consists in reacting catechol with isobutyraldehyde, with the attendant formation of an intermediate, the 2-isopropyl-1,3-benzodioxol, which is subsequently isomerized on a catalyst based on magnesium chloride and palladium on charcoal, such as disclosed, for example, in the U.S. Pat. No. 4,118,400. This process, while providing an acceptable selectivity in the useful reaction product, is unsatisfactory due to its intricacy and the low conversion rating of its second reaction stage.

Therefore, an object of the present invention is to provide a process for the production of 2,3-dihydro-2,2-dimethyl-7-benzofuranol which is exempt, or substantially so, from the above indicated shortcomings.

The process according to the present invention essentially comprises the preliminary reaction between 4-tert.butyl catechol, or catechol, and isobutyraldehyde under the influence of specially provided catalysts and the subsequent contact of the products thus obtained with catalytic amounts of one or more compounds having an acidic nature and an optional final treatment in order to obtain the expected product.

DESCRIPTION OF THE INVENTION

According to the present invention, the process for the preparation of 2,3-dihydro-2,2-dimethyl-7-benzofuranol can be differently embodied according to whether 4-tert.butyl catechol, or catechol as such, is selected as the starting compound.

Therefore, in the case in which 4-tert.butyl catechol and isobutyraldehyde are reacted together, the process can be split into the following steps:

In a first reaction stage, 4-tert.butyl catechol and isobutyraldehyde are contacted in a molar ratio of the former to the latter equal to at least 0.3:1 and the working temperature is from 80° C. to 200° C., under the influence of catalytic amounts of at least one compound which is a member selected from the group consisting of the oxides, the hydroxydes, the alcoholates and the carboxylates of metals belonging to the Groups IA, IIA, IIB and VIIB of the Periodic System of the Elements, in the optional presence of an inert (nonreactive) liquid organic solvent which is inactive over the other components of the reaction medium, to give a mixture of the intermediates, viz. 1,1-bis(2,3-dihydroxy-5-tert.butylbenzene)-dimethyl ethane, and 4-tert.butyl-6-isobutenylcatechol;

In a second reaction stage, the mixture of reactants originated in the first stage is subjected to rearrangement, by contacting such a mixture, optionally stripped of the inert solvent and the unreacted isobutyraldehyde, with catalytic amounts of at least one compound having an acidic nature, either of an organic or an inorganic nature, working at a temperature of from 180° C. to 250° C. and under a pressure which is such as to vaporize the rearrangement products, viz. 2,3-dihydro-2,2-dimethyl-5-tert.butyl-7-benzofuranol and 4-tert.butyl catechol as they are being formed;

2,3-dihydro-2,2-dimethyl-5-tert.butyl-7-benzofuranol is separated and recovered from said vaporized compounds and, in a third reaction stage, 2,3-dihydro-2,2-dimethyl-5-tert.butyl-7-benzofuranol is catalytically dealkylated to 2,3-dihydro-2,2-dimethyl-7-benzofuranol.

The reactions which lead to the formation of the expected reaction products can be summarized by the following reaction pattern:

1st Step:

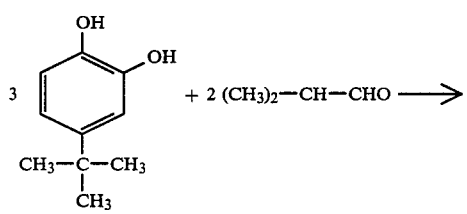

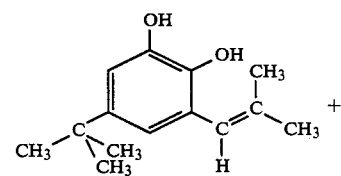

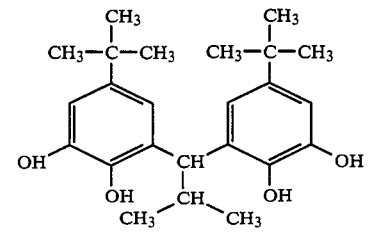

2nd Step:

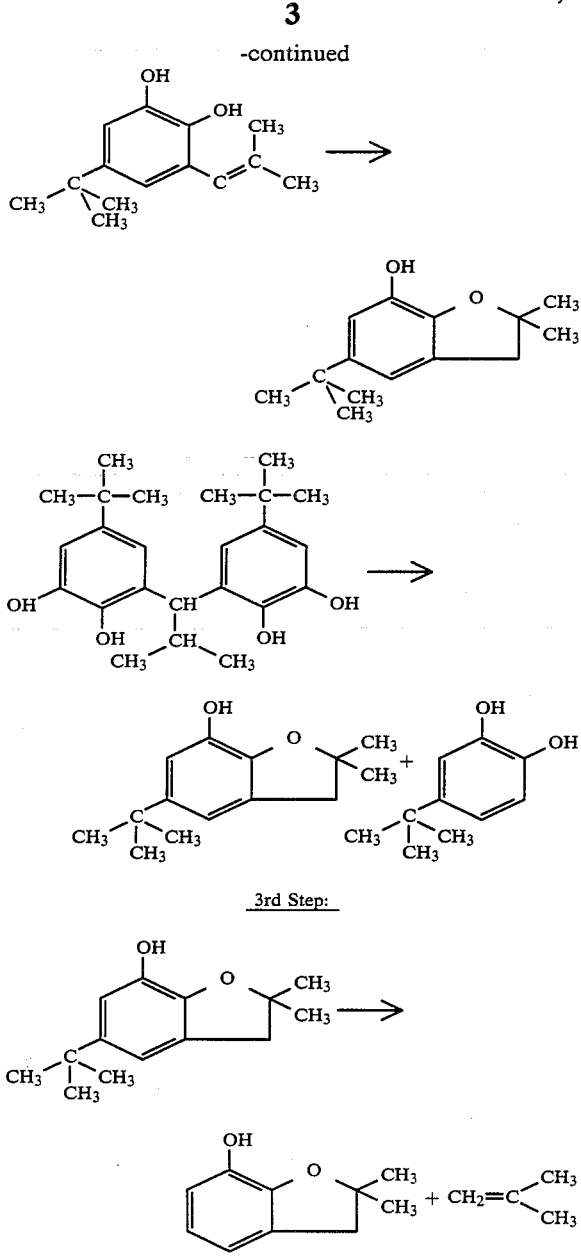

1st Step:

In the first reaction step, according to the present invention, molar ratios of 4-tert.butyl catechol to isobutyraldehyde from 0.3:1 to 2:1 are adopted, the preferred range being from 0.4:1 to 1:1.

The catalysts which are best preferred for the first reaction stage are the oxides, hydroxydes, alcoholates and carboxylates of sodium, calcium, magnesium, zinc and manganese. Examples of such catalysts are sodium methylate and calcium oxide. These catalysts unfold their activity in amounts of from 0.3% to 10% by weight relative to 4-tert.butyl catechol, the preferred range being from 0.5% to 9% by weight. The reaction temperature may generally vary from 80° C. to 180° C. and the preferred range is from 110° C. to 160° C. The relative reaction times vary as a function of the temperature and the catalyst which have been selected and generally range from 1 hour to 10 hours.

The first reaction stage can be carried out without adding any organic solvents, so as to achieve a higher output for a certain useful volume of the reactor.

According to another embodiment of the present invention the first reaction stage is carried out in the presence of a liquid organic inert (nonreactive) solvent which is inactive under the working conditions. Examples of solvents which are useful to the purpose are the hydrocarbons, the alcohols, the ethers and the nitriles.

The water which is formed as a byproduct in the first reaction stage can be removed continually as it is being formed, from the reaction mass. According to a preferred embodiment, water is continually removed by azeotropic distillation with the organic solvent which is used as the reaction medium.

The reaction mixture which has been originated in the first reaction step can be used as such for the rearrangement reaction of the second stage. According to a preferred embodiment, such mixture is previously stripped of the solvent, if any, and of the unreacted isobutyraldehyde, by distilling off such compounds.

2nd Step:

In the second reaction step the reaction mixture coming from the first step, and possibly stripped of the compounds aforementioned, is contacted with catalytic amounts of at least one compound of an organic or a mineral nature having an acidic nature. The catalysts suitable to this purpose can be selected from among sulphuric, phosphoric acids, potassium bisulphate, acidic alumina, acidic zeolite and p.toluenesulphonic acid. Above all these, phosphoric acid (H₃PO₄) is preferred, or aqueous phosphoric acid having a concentration of from 50% to 100%, on account of its outstanding stability under the reaction conditions.

The quantity of added catalyst must, at any rate, be stoichiometrically higher than the amount of catalyst as used in the first reaction step. Useful amounts of catalyst for the second reaction step are generally comprised in the range of from 1% to 10% by weight relative to the reaction intermediate originated in the first step, in addition to the quantity which is required to neutralize said catalysts of the first step. The preferred values for the catalysts of the second step are in the range of from 2% to 5% by weight relative to the intermediates aforementioned. The reaction temperatures in the second step range from 180° C. to 250° C., the preferred range being from 200° C. to 250° C.

According to an important aspect of the process according to the present invention, the products of the rearrangement, that is, 2,3-dihydro-2,2-dimethyl-5-tert.-butyl-7-benzofuranol and 4 tert.-butyl catechol are removed from the reaction mass in vapour form, continually as they are being formed. Thus the reaction is carried out under reduced pressures so as to make a thorough removal possible. On account of the temperatures indicated above, the pressural values which are useful to the intended purposes range from 5 mmHg to 50 mmHg.

3rd Step:

The dealkylation of 2,3-dihydro-2,2-dimethyl-5-tert.-butyl-7-benzofuranol is preferably carried out on said compound after that it has been separated from 4-tert.-butylcatechol.

More particularly, the dealkylation is carried out by heating to a temperature of about 200° C. the 2,3-dihydro-2,2-dimethyl-5-tert.butyl-7-benzofuranol in the presence of an amount of from 3% to 10% by weight of a dealkylation catalyst which is a member selected from the group consisting of acidic aluminas and phosphoric acid.

In practice, the operation is conducted by distilling in a continuous run 2,3-dihydro-2,2-dimethyl-7-benzofuranol out of the medium in which said dealkylation is effected.

When instead, catechol is used as the starting product, the procedure for preparing 2,3-dihydro-2,2-dimethyl-7-benzofuranol can be split into the following steps:

catechol and isobutyraldehyde are contacted, in the first reaction step, in a molar ratio of the former to the latter equal to at least 1:1 and the working temperature is from 80° C. to 180° C., under the influence of catalytic amounts of at least one compound selected from the group consisting of the oxides, hydroxides, alcoholates and carboxylates of metal belonging to the Groups IA, IIA, IIB and VIIB of the Periodic System of the Elements, in the optional presence of a liquid organic solvent which is inert, that is nonreactive, towards the other components of the reaction medium, to produce the intermediate compound 1,1-bis(2,3-dihydroxybenzene)dimethyl ethane.

there are separated, if so desired, one or more low-boiling compounds from the reaction mixture of the first step;

said intermediate coming from the first step is subjected to a rearrangement reaction in a second reaction step, in the relative reaction mixture which has been stripped, if so desired, of one or more low-boiling compounds, by contacting said mixture with catalytic amounts of at least one compound of either an organic or a mineral nature and having acidic properties, by working at a temperature of from 180° C. to 250° C. and under such a pressure as to vaporize the rearrangement products as the latter are being formed;

2,3-dihydro-2,2-dimethyl-7-benzofuranol is separated and recovered from said vaporized rearrangement products.

The reactions which lead to the formation of 2,3-dihydro-2,2-dimethyl-7-benzofuranol, according to the present invention, can be summarized by the following reaction pattern:

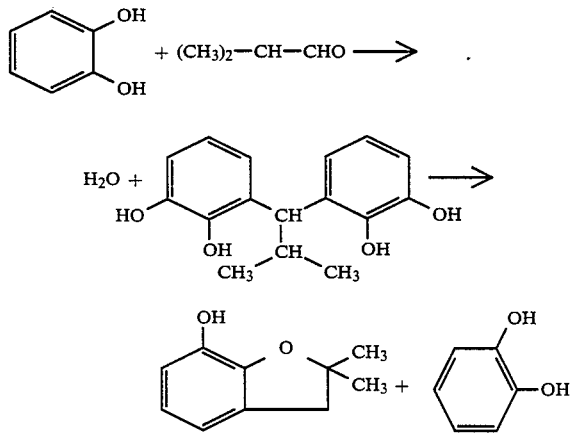

1st Step:

According to the present invention, there are used, in the first reaction step, molar ratios of catechol to isobutyraldehyde of from 1:1 to 3:1, the preferred range being about 2:1.

The best preferred catalysts for the reaction of the first step are the oxides, hydroxides, alcoholates, and carboxylates of sodium, calcium, magnesium, zinc and manganese. Examples of such catalysts are calcium oxide, sodium methylate and zinc acetate. These catalysts unfold their action in an amount of from 0.2% to 5% by weight relative to catechol, the preferred range being of from 0.3% to 2.5% by weight.

The reaction temperatures may generally vary within a range of from 80° C. to 180° C., the preferred range being from 110° to 160° C.

The relative reaction times vary as a function of the temperature and the preselected catalyst are generally comprised within a range of from 1 hour to 10 hours.

The reaction of the first step can be carried out without any added organic solvent being present, so as to achieve a higher output for the same useful volume of the reactor.

According to another embodiment of the present invention, the first reaction step is carried out in the presence of a liquid organic solvent which is inert, that is non reactive, in the working conditions. Examples of solvents which are useful to the intended purpose are the hydrocarbons, the alcohols, the ethers and the nitriles.

The water which is formed as a byproduct of the first reaction step can be continually removed as it is being formed, from the reaction mass. According to a preferred embodiment, the water is continually removed by azeotropic distillation with the organic solvent which has been used as the reaction medium.

The reaction mixture coming from the first step, can be used as such for the rearrangement reaction of the second stage, or, as an alternative, it can be previously subjected to the separation of one or more low-boiling compounds, such as water, solvent and unreacted isobutyraldehyde and catechol.

2nd Step:

In the second reaction step, the reaction mixture, coming from the first step and stripped, if so desired, of one or more low-boiling components, is contacted with catalytic amounts of at least one compound of an organic or mineral origin and of an acidic nature. The catalysts adapted to the purpose can be selected from among sulphuric acid, phosphoric acid, potassium bisulphate, acidic alumina, acidic zeolite and p.toluenesulphonic acid. Above all, phosphoric acid ($H_3PO_4$) is preferred, or the aqueous phosphoric acid having a concentration of from 50% to 100%, due to its outstanding stability under the reaction conditions.

The amount of the added catalyst must, at any rate, be stoichiometrically higher than the quantity of catalyst used in the first reaction step. More particularly, said second step catalyst must be present in an amount of from 1% to 10% by weight relative to the intermediate originated in the first step, in addition to the quantity which is required to neutralize said first step catalyst. Preferred values of the concentration of the catalyst are in the range of from 2% to 5% relative to the intermediate aforesaid.

The reaction temperatures of the second step range from 180° to 250° C., the preferred values being in the range from 200° C. to 250° C.

According to an important aspect of the process according to this invention, the products of the rearrangement, catechol and 2,3-dihydro-2,2-dimethyl-7-benzofuranol, are removed from the reaction mass, in vapour form and continually as they are being formed. Therefore, the reaction is carried out under a reduced pressure so as to make a through removal possible. In view of the temperatures suggested above, the values of the pressure which are useful to the purpose range from 10 mmHg to 50 mmHg.

The reaction products thus obtained are condensed and subsequently subjected to the conventional separation and purification treatments.

DESCRIPTION OF THE SPECIFIC EMBODIMENTS

The experimental examples which follow are illustrative and do not limit the invention.

EXAMPLES 1–6

(4-tert.butyl-catechol)

Example 1 (First Step)

A 250-ml flask, equipped with a magnetic drive stirrer and a reflux system of the Marcusson type is charged with 71.4 g (0.43 mol) of 4-tert.butyl catechol, 86 mls (68.3 g, i.e. 0.95 mol) of isobutyraldehyde, 6.4 g (0.118 mol) of sodium methylate and 160 mls of toluene.

The mixture is brought to a boil (about 120° C.) under ambient pressure and water is azeotropically removed as it is being formed as a reaction byproduct. The reaction is stopped after about 9 hours, when about 6 mls of water have been separated.

Toluene and unreacted isobutyraldehyde are now distilled off from the reaction mixture.

The residual reaction mixture thus obtained has the following composition:

4-tert.butyl catechol: 0.003 mol, 4-tert.butyl-6-isobutenylcatechol: 0.024 mol, and 1,1-bis(2,3-dihydroxy-5-tert.butylbenzene)-dimethylethane: 0.08 mol.

The last named compound has a melting point of 177° C.

The identity of the products enumerated above is established by gas-liquid chromatography, mass spectrometry, infrared analysis and NMR.

Example 2 (First Step)

A 500-ml flask, equipped with a magnetically driven stirrer and a Marcusson type reflux system, is charged with 249 g (1.5 mol) of 4-tert.butylcatechol, 170 mls (135 g, i.e. 1.87 mol) of isobutyraldehyde, 2 g (0.035 mol) of calcium oxide (CaO) and 200 mls of toluene. The mixture is brought to a boil (about 120° C.) under atmospherical pressure and water is withdrawn azeotropically as it is being formed as the reaction byproduct. The reaction is discontinued after about 9 hours, when about 16.5 mls of water have been removed. Toluene and the unreacted isobutyraldehyde are now distilled of from the reaction mixture. The raw reaction mixture thus obtained has the following composition:

4-tert.butylcatechol: 0.217 mol, 4-tert.butyl-6-isobutenylcatechol: 0.516 mol, and 1,1-bis(2,3-dihydroxy-5-tert.butylbenzene)-dimethylethane: 0.38 mol.

The last named compound has a melting point of 177° C. The identity of these compounds is established just as in the previous example.

Example 3 (Second Step)

The reaction raw product obtained in Example 1 is supplemented with 13.5 g of phosphoric acid (H$_3$PO$_4$) (100% conc.) whereafter the temperature of the external bath is gradually brought to 200° C. and the reaction products are distilled off as they are being formed, while maintaining a pressure of 5 mmHg.

During a period of 2 hours, there are distilled 0.0675 mol of 4-tert.butylcatechol and 0.309 mol of 2,3-dihydro-2,2-dimethyl-5-tert.butyl-7-benzofurnaol.

The last named product melts at 76° C. and boils at 130° C. (5 mmHg). The identity of these products is established by gas-liquid chromatography, NMR and mass spectrometry.

Example 4 (Second Step)

The reaction raw product obtained in Example 2 is supplemented with 10 g of phosphoric acid (H$_3$PO$_4$) (100% conc.) whereafter the temperature of the external bath is gradually raised to 210° C. and the reaction products are distilled off as they are being formed, while maintaining an absolute pressure of 5 mmHg. During a period of 2 hours, there are distilled 0.395 mol of 4-tert.buthylcatechol and 0.6 mol of 2,3-dihydro-2,2-dimethyl-5-tert.butyl-7-benzofuranol. The last named compound melts at 76° C. and boils at 130° C. (5 mmHg). The identity of these products is established just as in the previous example.

Example 5 (Third Step)

A 50-ml flask, equipped with a magnetically driven stirrer, is charged with 40 g (0.182 mol) of 2,3-dihydro-2,2-dimethyl-5-tert.butyl-7-benzofuranol (obtained in the previous examples) and 4 g of acidic alumina, commercially known with the symbol HA-100 5P by the Company Akzo Chemie. The temperature of the external bath is raised to 200° C. and distillation is carried out with rectification under a pressure of 35 mmHg. A distillate is thus obtained (37 g) which consists for 72% by weight of 2,3-dihydro-2,3-dimethyl-7-benzofuranol, boiling point 120° C. (20 mmHg) and for 27% by 2,3-dihydro-2,2-dimethyl-5-tert.butyl-7-benzofuranol (unreacted). The selectivity of the dealkylation reaction is thus 96% relative to the converted compound.

Example 6 (Third Step)

A 50-ml flask equipped with a magnetically driven stirrer is charged with 40 g (0.182 mol) of 2,3-dihydro-2,2-dimethyl-5-tert.butyl-7-benzofuranol and 1.2 g of 100% phosphoric acid (H$_3$PO$_4$).

This mixture is subjected to heating and distillation just as in the previous example. Thus, a distillate is obtained (37 g) which contains 16% by weight of 2,3-dihydro-2,3-dimethyl-7-benzofuranol (boiling point 120° C. at 20 mmHg) and 83% by weight of 2,3-dihydro-2,2-dimethyl-5-tert.butyl-7-benzofuranol (unreacted).

The selectivity of the dealkylation reaction is thus about 95% relative to the converted compound.

EXAMPLES 7–9

(Catechol)

Example 7

A 250-ml steel autoclave, equipped with a magnetically driven stirrer, is charged with 165 g (1.5 mol) of catechol, 57.6 g (0.8 mol) of isobutyraldehyde and 0.6 g (0.01 mol) of calcium oxide (CaO), finely ground. The mixture is heated to 175° C. for 7 hours, with a vigorous stirring. The temperature is then lowered to 130° C. and water, a byproduct of the reaction is distilled off together with the unreacted isobutyraldehyde, and finally the pressure is reduced to about 10 mmHg and the unreacted catechol is distilled off. The residual mixture is supplemented with 85% phosphoric acid ($H_3PO_4$), whereafter the temperature is gradually raised to 240° C.-250° C. and the pressure is maintained at about 10 mmHg. During a period of about 4 hours, there are evaporated and recovered 43.5 g (0.27 mol) of 2,3-dihydro-2,2-dimethyl-7-benzofuranol, together with catechol. The overall quantity of recovered catechol is thus 118 g (1.07 mol), so that the conversion, calculated relatively to catechol, is 28.5% with a selectivity of 62% of the useful reaction product, which is 2,3-dihydro-2,2-dimethyl-7-benzofuranol.

Example 8

A 250-ml flask, equipped with a stirrer and a refluxing system with azeotropic removal of water (Marcusson) is charged with 110 g (1 mol) of catechol, 50 mls (39.6 g=0.55 mol) of isobutyraldehyde, 2.74 g (0.015 mol) of zinc acetate and 30 mls of toluene. The mixture is brought to a boil (about 120° C.) during about 7 hours, during which about 10 mls of water are withdrawn. From the reaction mixture there are now separated by distillation toluene and the unreacted isobutyraldehyde, working under a pressure of 30 mmHg. The residue of the distillation is supplemented with 7.0 g of 85%-phosphoric acid ($H_3PO_4$), whereafter the temperature is raised to 245° C. and the pressure is stabilized at 20 mmHg.

During a period of about 4 hours, there are evaporated and recovered 72.5 g (0.66 mol) of catechol and 21 g (0.13 mol) of 2,3-dihydro-2,2-dimethyl-7-benzofuranol. Thus, the conversion, based on catechol, is 34% with a selectivity of the useful reaction product 2,3-dihydro-2,2-dimethyl-7-benzofuranol equal to 37.5%.

Example 9

A 250-ml flask, equipped with a stirrer and a refluxing system with azeotropic water elimination is charged with 165 g (1.5 mol) of catechol, 85 mls (67.32 g=0.93 mol) of isobutyraldehyde, 1 g (0.018 mol) of calcium oxide (CaO) and 40 mls of toluene.

The mixture is brought to a boil (about 120° C.) for about 8 hours, in the course of which about 14 mls of water are removed.

From the reaction mixture there are distilled off, then, toluene and the unreacted isobutyraldehyde, working under an absolute pressure of 30 mmHg. The distillation residue is supplemented with 9.4 g of 85%-phosphoric acid ($H_3PO_4$), whereafter the temperature is raised to 245° C., and pressure stabilized at 20 mmHg. During a time of about 4 hours, there are evaporated and recovered 92 g (0.84 mol) of catechol and 50 g (0.31 mol) of 2,3-dihydro-2,2-dimethyl-7-benzofuranol.

Thus, the conversion rating based on catechol is 55.7%, and the selectivity of the useful reaction product, i.e. 2,3-dihydro-2,2-dimethyl-7-benzofuranol is 46%.

We claim:

1. A process for the preparation of 2,3-dihydro-2,2-dimethyl-7-benzofuranol, comprising the steps of:
    (a) contacting in a first reaction stage 4-tert. butyl catechol and isobutyraldehyde in a molar ratio from 0.3:1 to 2:1, in the presence of from 0.3 to 10 percent by weight, relative to the 4-tert.butyl catechol, of at least one catalytic compound selected from among oxides, hydroxides, alcoholates and carboxylates of metals belonging to the Groups IA, IIA, IIB and VIIB of the Periodic System of the Elements, at a temperature from 80° to 180° C., while removing by-product water as it is formed, to produce the intermediates 1,1-bis(2,3-dihydroxy-5-tert.butylbenzene)dimethyl ethane and 4-tert.butyl-6-isobutenylcatechol,
    (b) subjecting to rearrangement in a second reaction stage the reaction mixture obtained, stripped of unreacted isobutyraldehyde, by contacting said reaction mixture with from 1 to 10 percent by weight, relative to the intermediates, of at least one catalytic acidic compound at a temperature from 180° to 250° C. and under a pressure equivalent to from 5 to 50 mm of mercury, while continuously removing by vaporization the rearrangement products 2,3-dihydro-2,2-dimethyl-5-tert-butyl-7-benzofuranol 4-tert-butyl catechol as they are formed, and
    (c) recovering 2,3-dihydro-2,2-dimethyl-5-tert.butyl-7-benzofuranol from the vaporized products and dealkylating said compound in a third reaction stage in the presence of from 3 to 10 percent by weight of a catalyst selected from among acidic aluminas and phosphoric acid to obtain 2,3-dihydro-2,2-dimethyl-7-benzofuranol.

2. Process according to claim 1, in which the step (b) catalyst is selected from among sulphuric acid, phosphoric acid, potassium bisulphate, acidic alumina, acidic zeolite and p-toluenesulphonic acid.

3. A process according to claim 1, in which for step (a) the molar ratio of tert.butyl catechol to isobutyraldehyde is from 0.4:1 to 1:1.

4. A process according to claim 1, in which the catalyst for step (a) is selected from among oxides, hydroxides, alcoholates and carboxylates of sodium, calcium, magnesium, zinc and manganese.

5. A process according to claim 4, in which the catalyst for step (a) is selected from the group consisting of sodium methylate and calcium oxide.

6. A process according to claim 1, in which the step (a) catalyst is used in an amount from 0.5 to 9 percent by weight, relative to the weight of 4-tert.butyl catechol.

7. A process according to claim 1, in which the step (a) reaction is conducted at a temperature from 110° to 160° C.

8. A process according to claim 1, in which the reaction in step (a) is carried out in the presence of a solvent selected from among hydrocarbons, alcohols, ethers and nitriles.

9. A process according to claim 1, in which the phosphoric acid has a concentration from 50 to 100 percent.

10. A process according to claim 9, in which the step (b) catalyst is used in an amount from 2 to 5 percent by weight, relative to the intermediates.

11. A process according to claim 1, in which the step (b) reaction is conducted at a temperature from 200° to 250° C.

12. A process for the preparation of 2,3-dihydro-2,2-dimethyl-7-benzofuranol comprising:
    (a) contacting in a first reaction stage catechol and isobutyraldehyde, in a molar ratio equal to at least 1:1 and at a temperature from 80° C. to 180° C., in the presence of catalytic amounts of at least one compound selected from among oxides, hydroxides, alcoholates and carboxylates of metals belonging to Groups IA, IIA, IIB and VIIB of the Periodic System of the Elements, in the optional presence of an organic liquid solvent that is inert towards the other components of the reaction medium, to give the intermediate compound 1,1-bis(-dihydroxybenzene)dimethyl ethane;

(b) separating low boiling point compounds from the reaction mixture of the first stage;

(c) subjecting to rearrangement in a second reaction stage said intermediate formed in the first stage in the reaction mixture by contacting said mixture with catalytic amounts of at least one acidic compound at a temperature from 180° C. to 250° C. and under a pressure sufficient to vaporize the rearrangement products as they are being formed;

(d) separating and recovering said 2,3-dihydro-2,2-dimethyl-7-benzofuranol from said vaporized rearrangement products.

13. Process according to claim 12, characterized in that in the first stage the catalyst is present in an amount of from 0.2% to 5% by weight relative to catechol.

14. Process according to claim 12, characterized in that in the second stage one operates in the presence of a catalyst selected from among sulphuric acid, phosphoric acid, potassium bisulphate, acidic alumina, acidic zeolite and p-toluenesulphonic acid.

15. Process according to claim 12, characterized in that in the second stage one operates with an amount of catalyst of from 1% to 10% by weight relative to the intermediate compound obtained in the first stage.

* * * * *